US010518034B2

(12) United States Patent
Muller-Pathle

(10) Patent No.: US 10,518,034 B2
(45) Date of Patent: Dec. 31, 2019

(54) APPARATUS FOR CAPTURING AND PROCESSING IMAGES

(71) Applicant: SANOFI-AVENTIS DEUTSCHLAND GMBH, Frankfurt am Main (DE)

(72) Inventor: Stephan Muller-Pathle, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 15/324,539

(22) PCT Filed: Jul. 9, 2015

(86) PCT No.: PCT/EP2015/065671
§ 371 (c)(1),
(2) Date: Jan. 6, 2017

(87) PCT Pub. No.: WO2016/005485
PCT Pub. Date: Jan. 14, 2016

(65) Prior Publication Data
US 2017/0151390 A1   Jun. 1, 2017

(30) Foreign Application Priority Data
Jul. 10, 2014  (EP) ..................... 14176483

(51) Int. Cl.
*A61B 5/00*  (2006.01)
*A61M 5/31*  (2006.01)
(Continued)

(52) U.S. Cl.
CPC ........... *A61M 5/31* (2013.01); *A61B 5/14532* (2013.01); *A61B 5/4839* (2013.01); *A61M 5/24* (2013.01);
(Continued)

(58) Field of Classification Search
CPC .. A61M 5/31; A61M 5/31548; A61M 5/3202; A61M 2005/3126;
(Continued)

(56) References Cited

U.S. PATENT DOCUMENTS 9,852,321 B2 * 12/2017 Canini ............... G06K 7/10801
9,967,547 B2 *  5/2018 Georgiev ........... G02B 13/0065
(Continued)

FOREIGN PATENT DOCUMENTS

CN    1949833   4/2007
CN  102905613   1/2013
(Continued)

OTHER PUBLICATIONS

International Preliminary Report on Patentability in International Application No. PCT/EP2015/065671, dated Jan. 10, 2017, 6 pages.
(Continued)

*Primary Examiner* — Ali Bayat
(74) *Attorney, Agent, or Firm* — Fish & Richardson P.C.

(57) ABSTRACT

An apparatus comprising an optical sensor having a plurality of photosensitive cells arranged in a grid, wherein the optical sensor is configured to capture a first image using a first subset of the photosensitive cells and to capture a second image using a second subset of the photosensitive cells, the second subset not including any of the photosensitive cells in the first subset, wherein the apparatus is configured to process the first and second images using at least one optical character recognition algorithm.

20 Claims, 8 Drawing Sheets

Figure 1A:
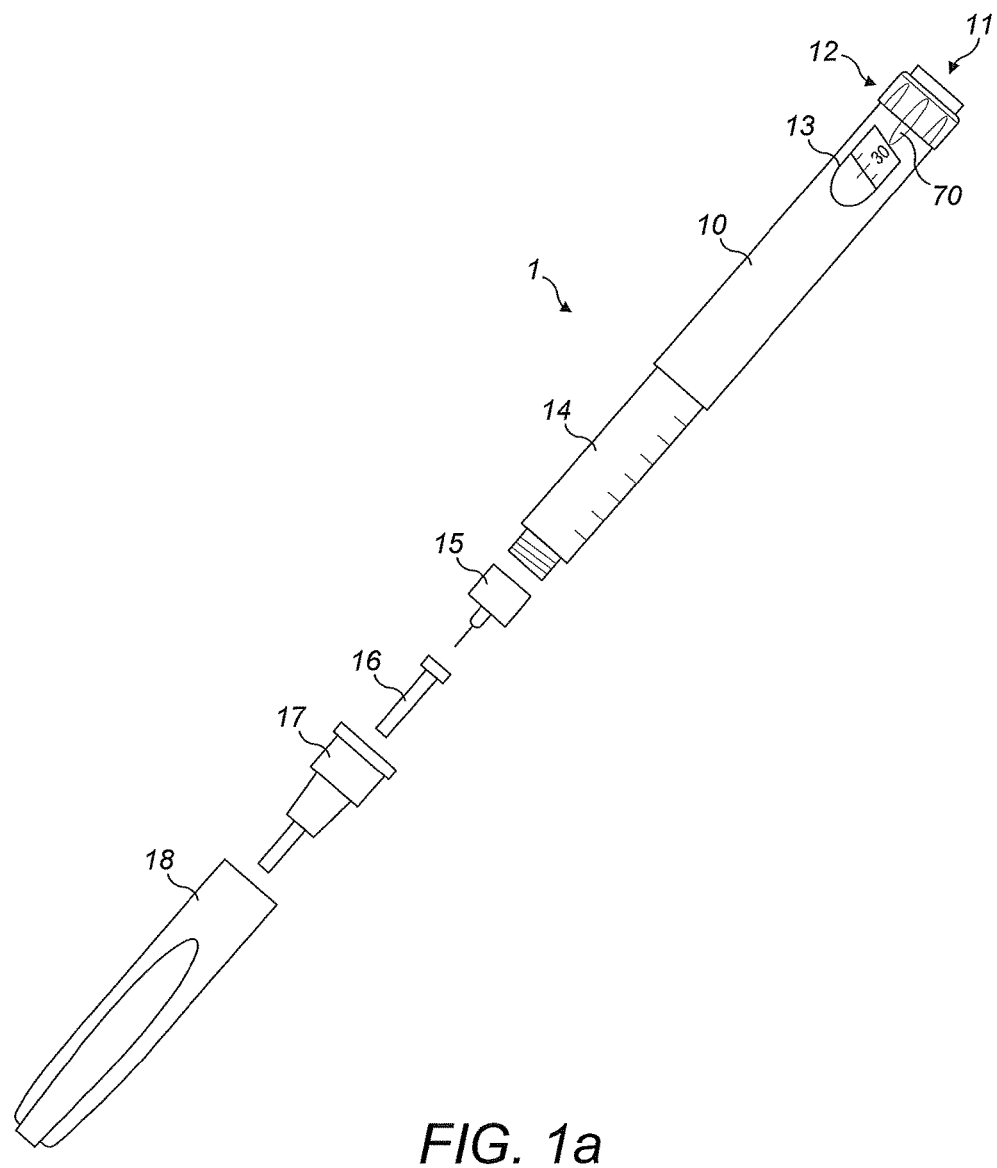

(51) Int. Cl.
  *A61M 5/24* (2006.01)
  *A61B 5/145* (2006.01)
  *G06F 19/00* (2018.01)
  *A61M 5/315* (2006.01)
  *G06K 9/62* (2006.01)
  *A61M 5/32* (2006.01)
  *G06K 9/18* (2006.01)

(52) U.S. Cl.
  CPC ...... *A61M 5/31548* (2013.01); *A61M 5/3202* (2013.01); *G06F 19/3468* (2013.01); *G06K 9/18* (2013.01); *G06K 9/6202* (2013.01); *G06K 9/6292* (2013.01); *A61M 2005/3125* (2013.01); *A61M 2005/3126* (2013.01); *A61M 2205/3306* (2013.01); *A61M 2205/3375* (2013.01); *A61M 2205/3584* (2013.01); *A61M 2205/3592* (2013.01); *A61M 2205/50* (2013.01); *A61M 2205/505* (2013.01); *A61M 2205/52* (2013.01); *A61M 2205/581* (2013.01); *A61M 2205/583* (2013.01); *A61M 2205/587* (2013.01); *A61M 2205/6063* (2013.01); *A61M 2205/8206* (2013.01); *A61M 2209/00* (2013.01); *A61M 2230/005* (2013.01); *A61M 2230/201* (2013.01); *G06K 2209/01* (2013.01)

(58) Field of Classification Search
  CPC .. A61M 2005/3375; A61M 2005/3584; A61M 2005/3592; A61M 2005/50; A61M 2005/505; A61M 2005/52; A61M 2005/581; A61M 2005/587; A61M 2230/005; A61M 2230/201; G06K 9/18; G06K 9/6202
  See application file for complete search history.

(56) References Cited

U.S. PATENT DOCUMENTS

| | | | | |
|---|---|---|---|---|
| 9,986,223 | B2* | 5/2018 | Goma | H04N 13/218 |
| 2007/0084927 | A1 | 4/2007 | Itou et al. | |
| 2010/0272360 | A1 | 10/2010 | Huang | |
| 2011/0267520 | A1* | 11/2011 | Pyanet | H04N 5/23212 348/296 |
| 2013/0038719 | A1* | 2/2013 | Canini | G06K 7/10732 348/135 |
| 2014/0028861 | A1* | 1/2014 | Holz | H04N 5/23277 348/208.4 |
| 2018/0218232 | A1* | 8/2018 | Tokuda | G06K 9/18 |

FOREIGN PATENT DOCUMENTS

| | | | | |
|---|---|---|---|---|
| EP | 2674181 | | 12/2013 | |
| JP | 2013-521963 | | 6/2013 | |
| WO | WO 2011/117212 | * | 9/2011 | ............ A61B 5/00 |
| WO | WO-2011117212 A1 | * | 9/2011 | |
| WO | WO 2013/010886 | | 1/2013 | |
| WO | WO 2013/024160 | | 2/2013 | |
| WO | WO 2014/061309 | | 4/2014 | |
| WO | WO 2014/095644 | | 6/2014 | |

OTHER PUBLICATIONS

International Search Report and Written Opinion in International Application No. PCT/2015/065671, dated Sep. 14, 2015, 9 pages.

* cited by examiner

APPARATUS FOR CAPTURING AND PROCESSING IMAGES

CROSS-REFERENCE TO RELATED APPLICATIONS

This application is a U.S. national stage application under 35 USC § 371 of International Application No. PCT/EP2015/065671, filed on Jul. 9, 2015, which claims priority to European Patent Application No. 14176483.7 filed on Jul. 10, 2014, the entire contents of which are incorporated herein by reference.

TECHNICAL FIELD

The present disclosure relates to an optical sensor and control system embodied in a supplemental device suitable for use with an injection device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen.

To be able to monitor insulin injection, for instance to prevent false handling of the insulin pen or to keep track of the doses already applied, it is desirable to measure information related to a condition and/or use of the injection device, such as for instance information on the injected insulin type and dose. This information is typically recorded manually by a user of the injection device. There is a need to reduce the user involvement in monitoring drug dose administration, both to reduce the burden on the user and the possibility of mistakes and to facilitate electronic storage and transmission of the data. Furthermore, if the drug dose is printed on a part of the injection device mechanism and viewed by a user through a dose window, it may be difficult for some users having poor eyesight to accurately determine the dose reading. This can lead to incorrect dose administration. There is therefore a need to make such injection devices easier to use for those having poor eyesight.

It has been described, for instance in WO 2011/117212 to provide a supplementary device comprising a mating unit for releasably attaching the device to an injection device. The device includes a camera and is configured to perform optical character recognition (OCR) on captured images visible through a dosage window of the injection pen, thereby to determine a dose of medicament that has been dialled into the injection device.

SUMMARY

A first aspect provides an apparatus comprising an optical sensor having a plurality of photosensitive cells arranged in a grid, wherein the optical sensor is configured to:

capture a first image using a first subset of the photosensitive cells; and capture a second image using a second subset of the photosensitive cells, the second subset not including any of the photosensitive cells in the first subset;

and wherein the apparatus is configured to process the first and second images using at least one optical character recognition algorithm.

The use of an apparatus so configured allows two images to be captured using a single optical sensor. However, the two images are distinct and separate and can be used to increase the reliability of the optical character recognition algorithm. In particular, where there are one or more defective photosensitive cells, having two separately captured images reduces the negative impact of these defects.

The first subset of photosensitive cells may comprise alternate lines of the grid and the second subset of photosensitive cells may comprise alternate lines of the grid. This allows two near identical images to be captured using a single optical sensor.

The first subset of photosensitive cells may comprise alternate columns of the grid and the second subset of photosensitive cells may comprise alternate columns of the grid. Alternatively, the first subset of photosensitive cells may comprise alternate rows of the grid and the second subset of photosensitive cells may comprise alternate rows of the grid. This allows two near identical images to be captured using a single optical sensor.

None of the photosensitive cells in the first subset may share an edge and none of the photosensitive cells in the second subset may share an edge. This also allows two near identical images to be captured using a single optical sensor.

Capturing and processing two near identical images simultaneously increases the resilience of the system, in particular to pixel defects.

The optical sensor may be configured to capture the first and second images simultaneously. This is possible where none of the photosensitive cells in the first and second subsets are the same. This minimises the time required to perform the image capture process.

The apparatus may be configured to:
process the first image using a first optical character recognition algorithm to produce a first result; and
process the second image using a second optical character recognition algorithm to produce a second result.

Using two different optical character recognition algorithms to process the first and second images increases the resilience of the system. Since the first and second images will be nearly identical, the result returned form both optical character recognition algorithms should be the same.

Each of the first and second optical character recognition algorithms may produce a confidence value in their respective results and the apparatus may be configured to combine the confidence values from the first optical character recognition algorithm and the second optical character recognition algorithm to produce a combined confidence value.

The apparatus may be configured to compare the first and second results and, when the results are the same, cause the result to be displayed on a display of the apparatus.

The apparatus may be configured, if the first and second results are not the same, to cause the optical sensor to capture a new first image using the first subset of the photosensitive cells, and to capture a new second image using the second subset of the photosensitive cells.

The apparatus may be configured to process the new first image using the second optical character recognition algorithm and process the new second image using the first optical character recognition algorithm.

The apparatus may comprise a processor which is configured to process the first and second images using at least one optical character recognition algorithm.

The apparatus may be a supplementary device for attachment to a drug delivery device.

A second aspect provides a method of operating an apparatus comprising an optical sensor having a plurality of photosensitive cells arranged in a grid, the method comprising:

capturing a first image using a first subset of the photosensitive cells;
capturing a second image using a second subset of the photosensitive cells, the second subset not including any of the photosensitive cells in the first subset; and
processing the first and second images using at least one optical character recognition algorithm.

The method may further comprise:
processing the first image using a first optical character recognition algorithm to produce a first result; and
processing the second image using a second optical character recognition algorithm to produce a second result.

BRIEF DESCRIPTION OF THE FIGS.

Figure 1B:
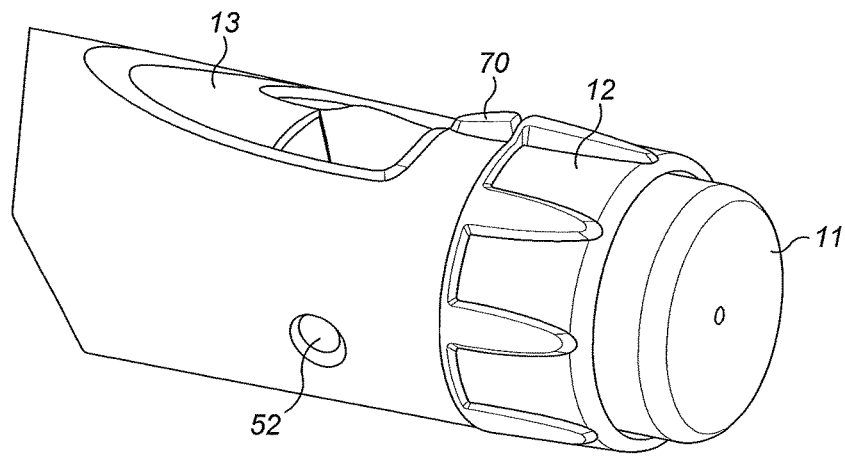
Figure 2A:
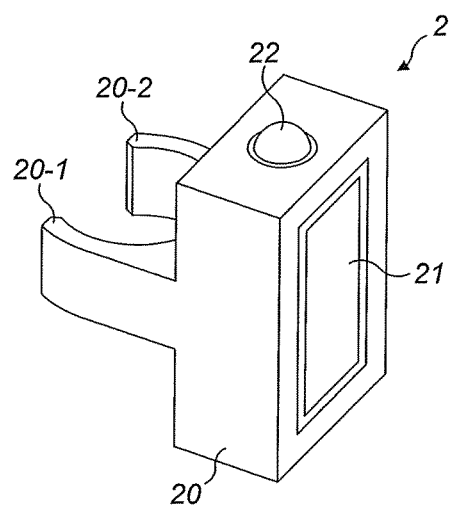
Figure 2B:
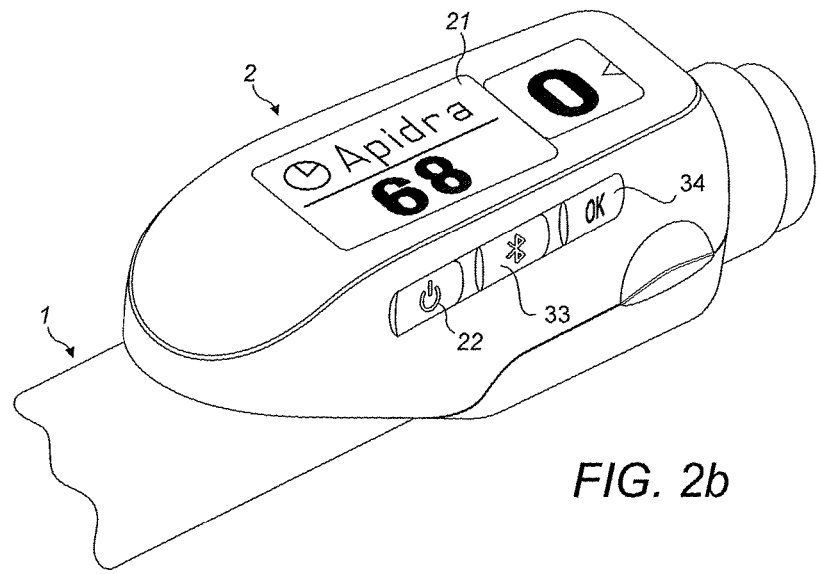
Figure 2C:
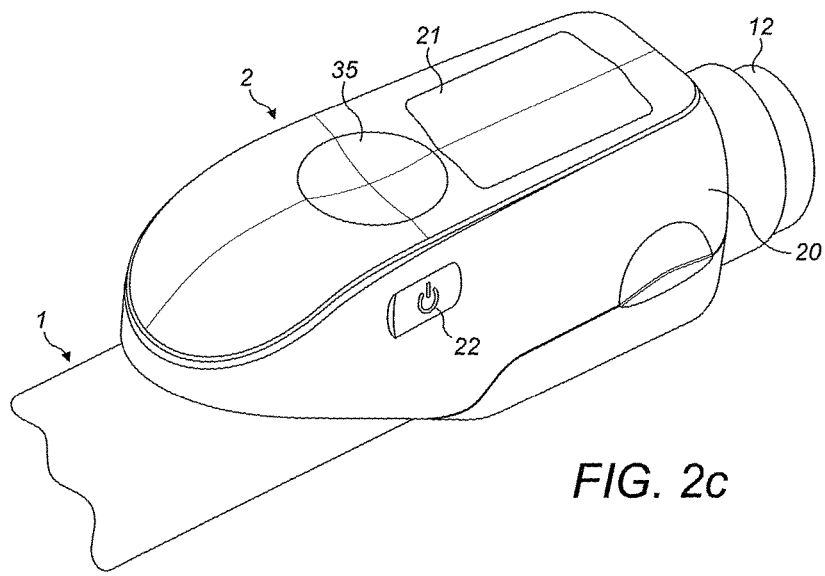
Figure 3A:
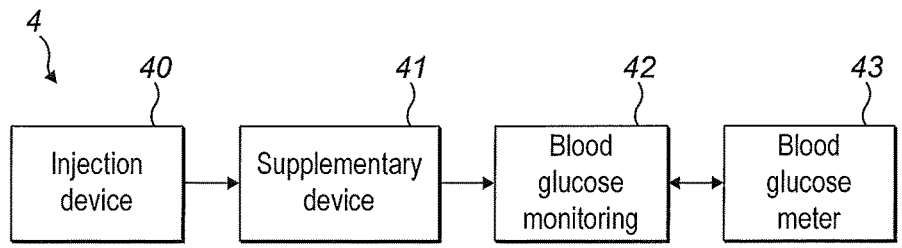
Figure 3B:
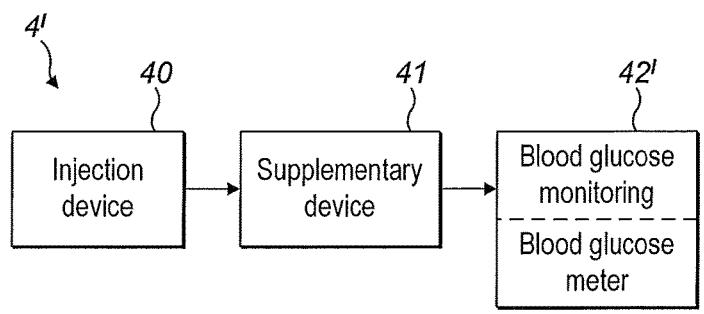
Figure 4:
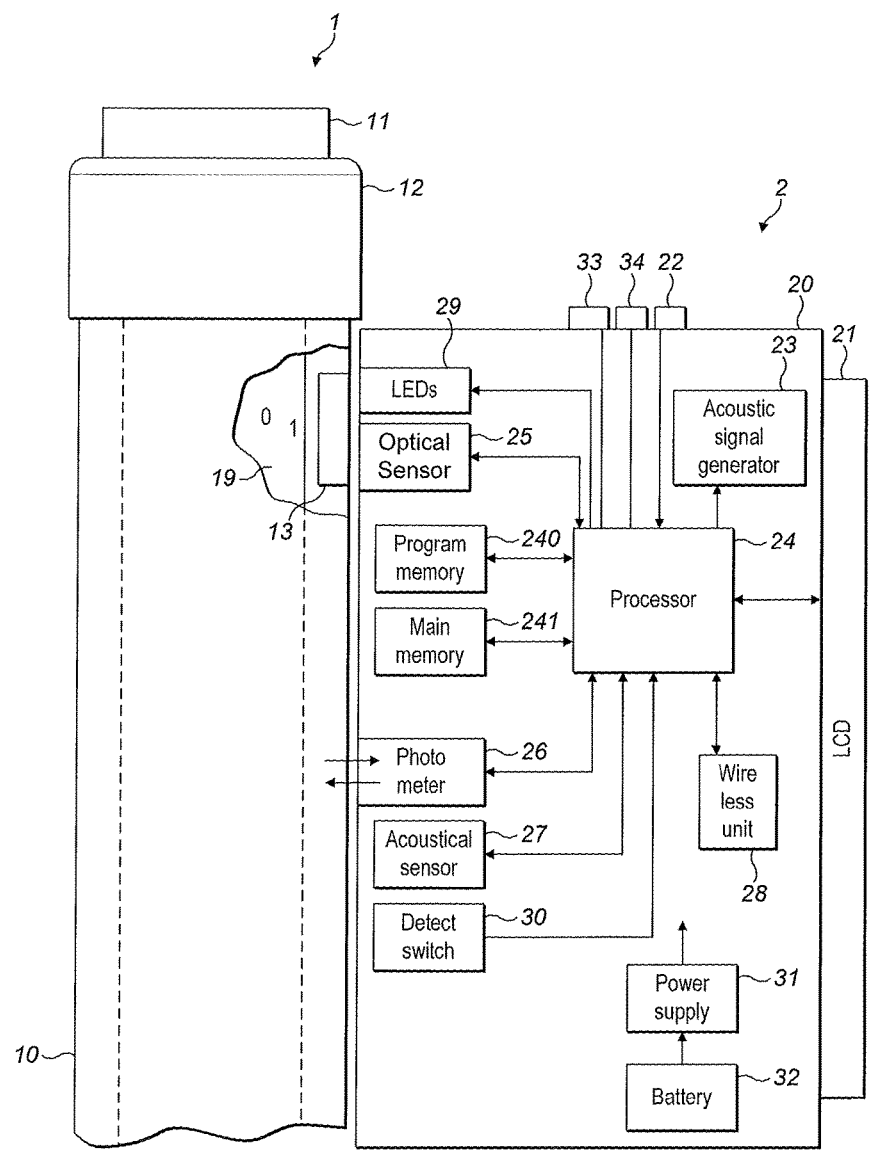
Figure 5:
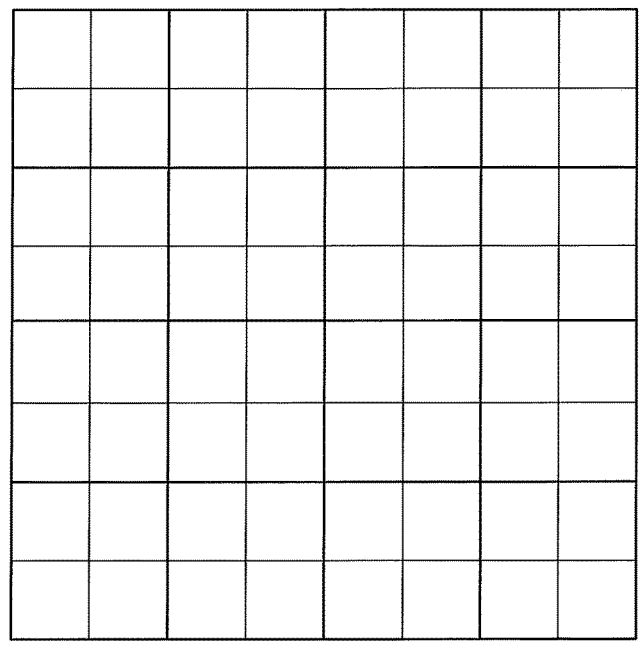
Figure 6A:
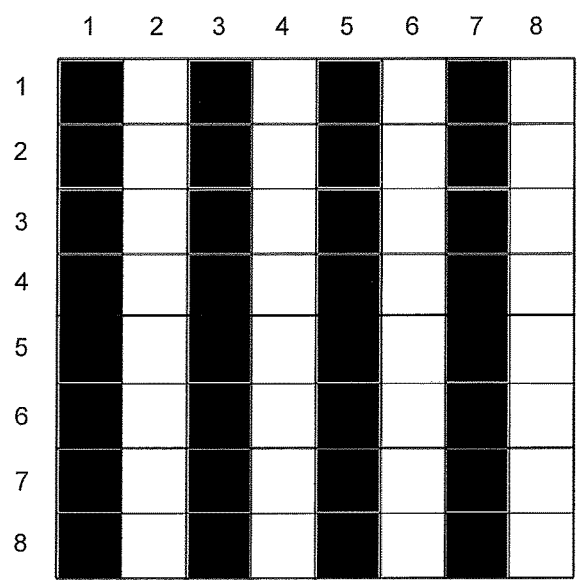
Figure 6B:
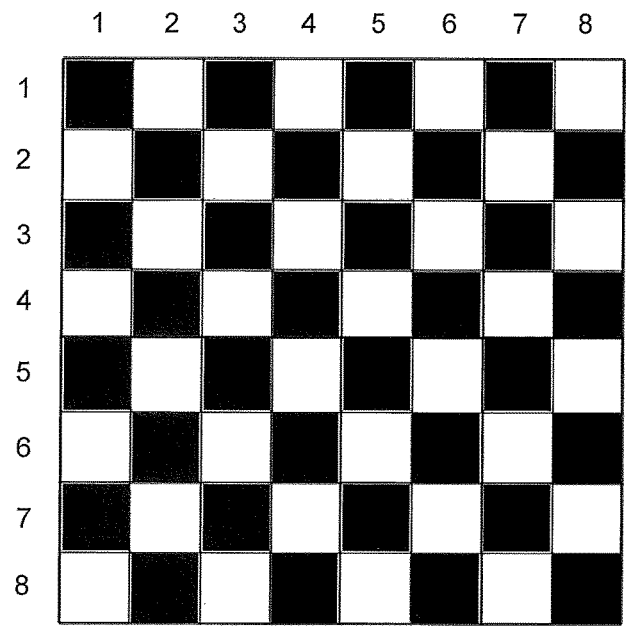
Figure 7:
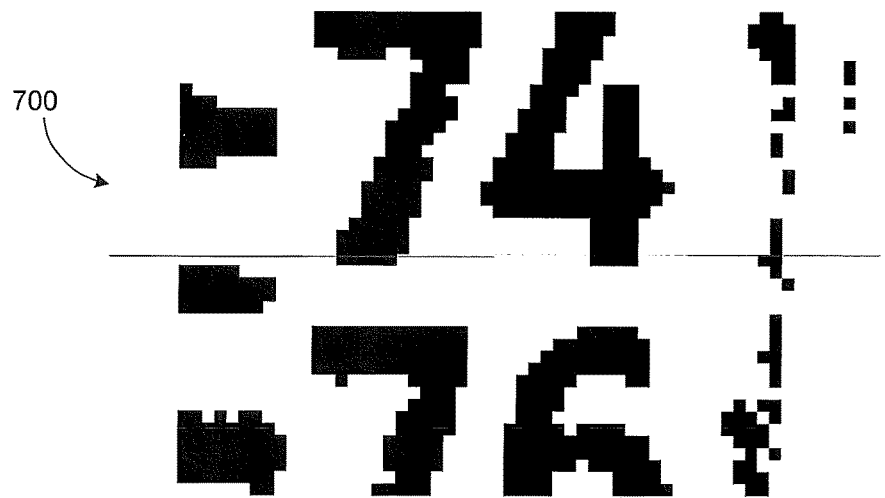
Figure 8:
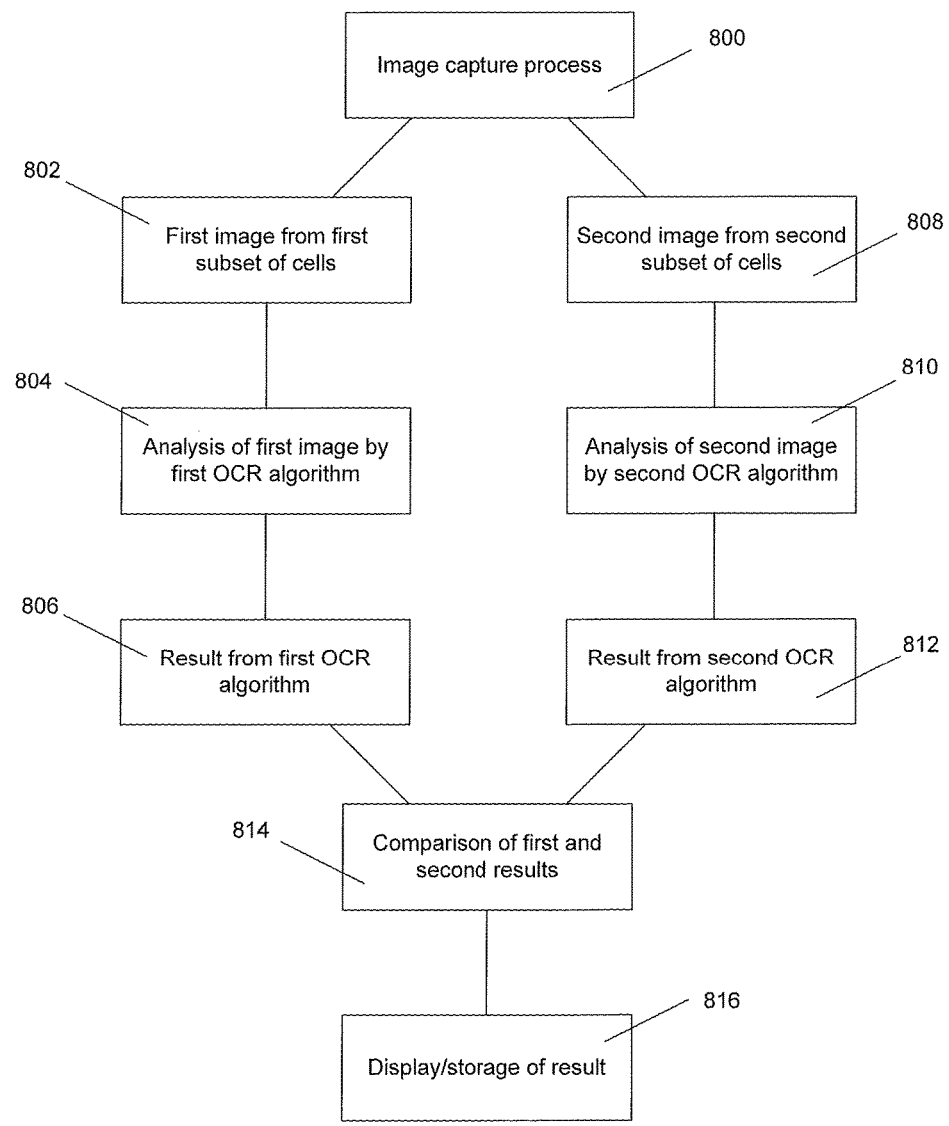

Embodiments will now be described, by way of example only, with reference to the accompanying drawings, in which:

FIG. 1a shows an exploded view of an injection device;
FIG. 1b shows a perspective view of some detail of the injection device of FIG. 1a;
FIG. 2a shows a schematic illustration of a supplementary device to be releasably attached to the injection device of FIG. 1;
FIG. 2b shows a perspective view of a supplementary device to be releasably attached to the injection device of FIG. 1;
FIG. 2c shows a perspective view of a supplementary device to be releasably attached to the injection device of FIG. 1;
FIGS. 3a and 3b show possible distributions of functions among devices when using a supplementary device (such as the supplementary devices of FIGS. 2a, 2b and 2c) together with an injection device;
FIG. 4 shows a schematic view of the supplementary device of FIG. 2a in a state where it is attached to the injection device of FIG. 1;
FIG. 5 shows schematically a portion of an optical sensor according to aspects of the disclosure;
FIGS. 6a and 6b illustrate operation of the optical sensor shown in FIG. 5;
FIG. 7 shows a typical post-binarization image of a dose window of the injection device of FIGS. 1a and 1b; and
FIG. 8 is a flow chart illustrating exemplary operation of an embodiment of the disclosure;

DETAILED DESCRIPTION

In the following, embodiments will be described with reference to a supplementary device for use with an insulin injection device. In particular, some aspects are described as being embodied in a supplementary device for temporary attachment to an insulin injection device so as to read insulin dose values dialled into the device. The present disclosure is however not limited to such application and may equally well be deployed with injection devices that eject other medicaments, or with other types of medical devices or non-medical devices having printed or otherwise displayed symbols which can be read by the apparatus of the present disclosure.

FIG. 1a is an exploded view of an injection device 1, which may be used in conjunction with the apparatus of the present disclosure. The injection device 1 may for instance represent Sanofi's Solostar (R) insulin injection pen.

The injection device 1 of FIG. 1a is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1a. It should be noted that the selected dose may equally well be displayed differently, for instance by means of an electronic display.

Turning the dosage knob 12 causes a mechanical click sound to provide acoustical feedback to a user. The numbers displayed in dosage window 13 are printed on a sleeve that is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

FIG. 1b shows a perspective view of the dose button end of the injection device 1. The injection device has a guiding rib 70 located on the housing 10 adjacent the dosage knob 12. The injection device 1 also has two indents 52 located on the housing 10. These may be symmetrical in relation to the guiding rib 70. The guiding rib 70 and indents 52 act to secure a supplementary device (described in detail below) in the correct position on the injection device 1.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to check that the needle is not blocked and to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to be ejected by the injection device. Nevertheless, differences (e.g. losses) between the ejected doses and the injected doses may of course be taken into account.

FIG. 2a is a schematic illustration of an embodiment of a supplementary device 2 to be releasably attached to injection device 1 of FIG. 1a. Supplementary device 2 comprises a housing 20 with a mating unit configured and embrace the housing 10 of injection device 1 of FIG. 1a, so that supplementary device 2 sits tightly on housing 10 of injection device 1, but is nevertheless removable from injection device 1, for instance when injection device 1 is empty and has to be replaced. FIG. 2a is highly schematic, and details of the physical arrangement are described below with reference to FIG. 2b.

Supplementary device 2 contains optical and optional acoustical sensors for gathering information from injection device 1. Information is displayed via display unit 21 of supplementary device 2. The dosage window 13 of injection device 1 is obstructed by supplementary device 2 when attached to injection device 1.

Supplementary device 2 further comprises three user input transducers, illustrated schematically as a button 22. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

FIG. 2b is a schematic illustration of a second embodiment of a supplementary device 2 to be releasably attached to injection device 1 of FIG. 1a. Supplementary device 2 comprises a housing 20 with a mating unit configured and embrace the housing 10 of injection device 1 of FIG. 1a, so that supplementary device 2 sits tightly on housing 10 of injection device 1, but is nevertheless removable from injection device 1.

Information is displayed via display unit 21 of supplementary device 2. The dosage window 13 of injection device 1 is obstructed by supplementary device 2 when attached to injection device 1.

Supplementary device 2 further comprises three user input buttons or switches. A first button 22 is a power on/off button, via which the supplementary device 2 may for instance be turned on and off. A second button 33 is a communications button. A third button 34 is a confirm or OK button. The buttons 22, 33, 34 may be any suitable form of mechanical switch. These input buttons 22, 33, 34 allow a user to turn on/off supplementary device 2, to trigger actions (for instance to cause establishment of a connection to or a pairing with another device, and/or to trigger transmission of information from supplementary device 2 to another device), or to confirm something.

FIG. 2c is a schematic illustration of a third embodiment of a supplementary device 2 to be releasably attached to injection device 1 of FIG. 1a. Supplementary device 2 comprises a housing 20 with a mating unit configured and embrace the housing 10 of injection device 1 of FIG. 1a, so that supplementary device 2 sits tightly on housing 10 of injection device 1, but is nevertheless removable from injection device 1.

Information is displayed via display unit 21 of the supplementary device 2. The dosage window 13 of injection device 1 is obstructed by supplementary device 2 when attached to injection device 1.

Supplementary device 2 further comprises a touch-sensitive input transducer 35. It also comprises a single user input button or switch 22. The button 22 is a power on/off button, via which the supplementary device 2 may for instance be turned on and off. The touch sensitive input transducer 35 can be used to trigger actions (for instance to cause establishment of a connection to or a pairing with another device, and/or to trigger transmission of information from supplementary device 2 to another device), or to confirm something.

FIGS. 3A and 3b show possible distributions of functions among devices when using a supplementary device (such as the supplementary devices of FIGS. 2a and 2b) together with an injection device.

In constellation 4 of FIG. 3a, the supplementary device 41 (such as the supplementary devices of FIGS. 2a and 2b) determines information from injection device 40, and provides this information (e.g. type and/or dose of the medicament to be injected) to a blood glucose monitoring system 42 (e.g. via a wired or wireless connection).

Blood glucose monitoring system 42 (which may for instance be embodied as desktop computer, personal digital assistant, mobile phone, tablet computer, notebook, netbook or ultrabook) keeps a record of the injections a patient has received so far (based on the ejected doses, for instance by assuming that the ejected doses and the injected doses are the same, or by determining the injected doses based on the ejected doses, for instance be assuming that a pre-defined percentage of the ejected dose is not completely received by the patient). Blood glucose monitoring system 42 may for instance propose a type and/or dose of insulin for the next injection for this patient. This proposal may be based on information on one or more past injections received by the patient, and on a current blood glucose level, that is measured by blood glucose meter 43 and provided (e.g. via a wired or wireless connection) to blood glucose monitoring system 42. Therein, blood glucose meter 43 may be embodied as a separate device that is configured to receive a small blood probe (for instance on a carrier material) of a patient and to determine the blood glucose level of the patient based on this blood probe. Blood glucose meter 43 may however also be a device that is at least temporarily implanted into the patient, for instance in the patient's eye or beneath the skin.

FIG. 3b is a modified constellation 4' where the blood glucose meter 43 of FIG. 3a has been included into blood glucose monitoring system 42 of FIG. 3a, thus yielding the modified blood glucose monitoring system 42' of FIG. 3b. The functionalities of injection device 40 and supplementary device 41 of FIG. 3a are not affected by this modification. Also the functionality of blood glucose monitoring system 42 and blood glucose meter 43 combined into blood glucose monitoring system 42' are basically unchanged, apart from the fact that both are now comprised in the same device, so that external wired or wireless communication between these devices is no longer necessary. However, communication between blood glucose monitoring system 42 and blood glucose meter 43 takes place within system 42'.

FIG. 4 shows a schematic view of the supplementary device 2 of FIG. 2a, b or c in a state where it is attached to injection device 1 of FIG. 1a.

A plurality of components are comprised within the housing 20 of supplementary device 2. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

In embodiments such as those shown in FIG. 2b, processor 24 interacts with a first button 22, via which supplementary device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplementary device 2.

In embodiments such as those shown in FIG. 2c, two of the buttons 33, 34 may be omitted. Instead, one or more capacitive sensors or other touch sensors are provided.

Processor 24 controls a display unit 21, which is presently embodied as a Liquid Crystal Display (LCD), but may be any other type of display device, for example an e-ink display. Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25 that is capable of capturing images of the dosage window 13, in which a currently selected dose is displayed (by means of numbers printed on the sleeve 19 contained in injection device 1, which numbers are visible through the dosage window 13). The optical sensor 25 may be further capable of recognizing characters (e.g. numbers) from the captured image and to provide this information to processor 24. Alternatively, The processor 24 is responsible for performing OCR on the captured images. The processor 24 may be configured to perform two or more different OCR processes which each use different algorithms.

Processor 24 also controls light-sources such as light emitting diodes (LEDs) 29 to illuminate the dosage window 13, in which a currently selected dose is displayed. A diffuser may be used in front of the light-sources, for instance a diffuser made from a piece of acrylic glass. Furthermore, the optical sensor may comprise a lens (e.g. an aspheric lens) which allows the field of view of the sensor 25 to encompass the whole of the dose window 13.

Processor 24 further controls a photometer 26, that is configured to determine an optical property of the housing 10 of injection device 1, for example a colour or a shading. The optical property may only be present in a specific portion of housing 10, for example a colour or colour coding of sleeve 19 or of an insulin container comprised within injection device 1, which colour or colour coding may for instance be visible through a further window in housing 10 (and/or in sleeve 19). Information on this colour is then provided to processor 24, which may then determine the type of injection device 1 or the type of insulin contained in injection device 1 (e.g. SoloStar Lantus with purple colour and SoloStar Apidra with blue colour). Alternatively, a camera unit may be used instead of photometer 26, and an image of the housing, sleeve or insulin container may then be provided to processor 24 to determine the colour of the housing, sleeve or insulin container by means of image processing. Further, one or more light sources may be provided to improve reading of photometer 26. The light source may provide light of a certain wavelength or spectrum to improve colour detection by photometer 26. The light source may be arranged in such a way that unwanted reflections, for example by dosage window 13, are avoided or reduced. In an example embodiment, instead of or in addition to photometer 26, a camera unit may be deployed to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance an expiration date).

Processor 24 further controls (and/or receives signals from) an acoustic sensor 27, which is configured to sense sounds produced by injection device 1. Such sounds may for instance occur when a dose is dialled by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by means of vibration.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Processor 24 receives an input from a pen detection switch 30, which is operable to detect whether the pen 1 is present, i.e. to detect whether the supplementary device 2 is coupled to the injection device 1.

A battery 32 powers the processor 24 and other components by way of a power supply 31.

The supplementary device 2 of FIG. 4 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system). The information may also be stored in the main memory 241 of the device 2.

FIG. 5 shows schematically a portion of an optical sensor which represents embodiments of the disclosure. Only a portion of the sensor is shown for ease of representation. Typically, the optical sensor 25 is chosen or designed so that it has a sufficient number of photosensitive cells (also referred to herein as photosensitive regions or pixels) to capture a single image of the number sleeve at sufficiently high resolution for an OCR process to be preformed with a desired level of accuracy. For example, a grid of 64×48 (horizontal×vertical) cells has typically been found to produce an image of sufficient resolution.

However, in the present disclosure, the number of photosensitive cells in either the horizontal or vertical direction is at least doubled. Referring to FIG. 5, and continuing with the example above, the optical sensor 25 may comprise a grid of 128×48 photosensitive cells. In this embodiment, the optical sensor 25 may be twice as wide, but have the same height as the typical sensor described above. As each photosensitive cell records incident light independently and sends signals independently, additional power and control circuitry is required to address each cell individually. The control circuitry is not shown for simplicity. Alternatively, the optical sensor 25 may comprise a grid of 64×96 photosensitive cells, i.e. the number of cells in the vertical direction has been doubled, with a corresponding increase in the vertical dimensions of the photosensitive cell array. The doubling of the number of photosensitive cells in one direction allows two near identical images to be captured using a single optical sensor, as will be described in more detail below.

FIGS. 6a and 6b illustrate operation of the optical sensor 25 shown in FIG. 5. The processor 24 is configured to control the optical sensor 25 to capture two separate images using different subsets of the photosensitive cells. Alternatively, the optical sensor 25 may be controlled to capture a single image and then to feed data from different subsets of pixels to the OCR algorithm, such that two separate images are analysed. As shown in FIG. 6a, the optical sensor 25 is controlled to capture a first image using the odd numbered columns (i.e. the first, third, fifth, etc.), illustrated by the black regions. The sensor 25 is controlled to capture a second image using the even numbered columns (i.e. the second, fourth, sixth, etc.), illustrated by the white regions. This produces two images of the device being viewed which are more or less identical, but independently produced. The two images may be captured simultaneously since none of the same photosensitive cells are being used, or one after the other.

In FIG. 6b, the photosensitive cells are grouped differently. The first subset of cells (black cells) comprises the odd numbered columns of the odd numbered rows and the even numbered columns of the even numbered rows. The second subset of cells (white cells) comprises the even numbered columns of the odd numbered rows and the odd numbered columns of the even numbered rows. As with the previously described embodiment, this produces two images of the device being viewed which are more or less identical, but independently produced. The two images may be captured simultaneously since none of the same photosensitive cells are being used, or one after the other. The OCR algorithms may be programmed to adjust for the misalignment in the odd and even numbered rows/columns respectively, for example by shifting the image data from some cells horizontally or vertically by a predetermined amount.

The quality of the images captured by the optical sensor 25 may be affected by the presence of defective cells. Since the images produced by the two subsets of photosensitive cells are more or less identical, the impact of a defective cell (or even a whole column or row of defective cells) in one of the subsets is greatly reduced.

The subsets described with reference to FIGS. 6a and 6b are equally applicable to an optical sensor 25 in which the number of cells in the vertical direction has been increased. For example, the first subset of cells may comprise the odd numbered rows while the second subset comprises the even numbered rows. Furthermore, the skilled person could devise different groupings of the cells, other than those shown in FIGS. 6a and 6b.

The processor 24 may use one or more algorithms to analyse the images and perform the OCR process. In some embodiments, both of the images produced are processed sequentially by a single OCR algorithm. In some other embodiments, the processor 24 is configured to perform two parallel OCR processes in order to provide redundancy and improve the confidence levels in the results obtained. In this case, each of the two images may be processed by a different one of the two algorithms. In yet further embodiments, each of the two images may be processed by both (or all) of the OCR algorithms. In any case, the symbol or symbols present in each of the two images are identified by the processor. The two results can then be compared by the processor to improve the confidence level in the results.

The OCR algorithms which are used to analyse the captured images have several steps. One suitable algorithm uses the following processes:

Defective and bad pixel correction
Light (exposure) correction
Distortion and slant correction
Binarization
Segmentation
Pattern matching For example, an exposure control algorithm rejects pictures that are too bright or too dark and a new picture is taken with adjusted exposure parameters. The numbers may be printed on a slant for ease of recognition and positioning by a human, but may be easier to decode if this slant is removed. The images captured by the optical sensor are typically greyscale images. These are converted to black and white images in the "Binarization" step. FIG. 7 shows a typical post-binarization image 700 of a dose window 13 of the injection device 1 which has been captured by the optical sensor 25. In some embodiments a fixed threshold is used to separate between black and white pixels. Pixels that have a value at or above the threshold become white, pixels below the threshold become black in the binarized picture. A high threshold will lead to artefacts (black parts in white areas), whereas a low threshold has the risk that in some cases parts of digits are missing. In tests, a sensor capable of detecting 256 grey values was used and a threshold value of 127 showed good results. The goal of the "Segmentation" step is to determine the exact location of each visible or partly visible symbol in the image. To achieve this, the algorithm defines the boundaries of the visible symbols by finding the edges of the symbols.

A pattern matching process is then performed to identify the symbols in the image. Templates for each symbol may be stored in a memory and the images are compared to these templates. In a straight forward approach the pattern matching could be performed on a pixel-by-pixel basis. However, this may require high computing power. Furthermore, this approach is prone to position variation between the image and the template. In some other embodiments, a feature recognition process is performed. Features may be horizontal, vertical or diagonal lines, curves, circles or closed loops etc. Such features may be recognized in the image and compared with templates.

The pattern matching part of the algorithm may alternatively be based on a vector comparison process. For example, the templates may be in the form of vectors describing the position and length of each line (continuous run) of black pixels relative to a vertical line extending through the centre of the template. The captured binary image of each symbol may similarly be converted into vectors and compared with each stored template in turn to find the best match. As well as outputting a result, the algorithm may also output a value representing the confident level of the result. Fro example, the result may be the number "18" and the confidence level may be 99.9%. The algorithm may also indicate the next most likely values and the confidence values in these results. For example, the next most likely result may be "10", with a confidence level of 0.05%.

The above description outlines one possible OCR algorithm. The image produced by the first subset of photosensitive cells may be processed by this OCR algorithm. The processor may be configured to run a different OCR algorithm, for example based on a Hidden Markov Model, and to process the image produced by the second subset of photosensitive cells using this different algorithm.

FIG. 8 shows a flow chart illustrating exemplary operation of the processor 24 in analysing the images captured by the optical sensor 25.

In step 800, the first and second images of the dose window 13 are captured by the optical sensor 25. The images may be captured simultaneously in a single image capture operation, since none of the same photosensitive cells are used in each of the two subsets. In step 802 the image data representing the first image is sent to the processor 24. In step 804 the processor 24 uses a first OCR algorithm to analyse the image data representing the first image. At step 806, the processor outputs the result of the first OCR algorithm. As described above, the result may also contain a confidence value. This confidence value may be based, for example, on the degree to which the number in the captured image can be matched with the stored template numbers.

In step 808 the image data representing the second image is sent to the processor 24. In step 810 the processor 24 uses a second OCR algorithm to analyse the image data representing the second image. At step 812, the processor outputs the result of the second OCR algorithm. As described above, the result may also contain a confidence value. Steps 808-812 may be performed concurrently with steps 802-806. Alternatively, steps 808-812 may be performed after steps 802-806.

In step 814, the results (and optionally confidence values) from the first and second OCR processes are compared to check that they correspond. The confidence values associated with each result may be aggregated to produce a new, increased confidence value. At step 816, provided that the first and second results correspond, the result is output for display on display 21 and/or storage in a memory of the device and/or transmission. If the results are not the same, or if the combined confidence value is below a threshold, the processor 24 may discard the result and control the optical sensor 25 to capture further images for analysis. The new images thus captured may be processed by the other of the two OCR algorithms that performed the initial analysis.

The invention claimed is:

1. A medical apparatus comprising:
    an optical sensor having a plurality of photosensitive cells arranged in a grid, wherein the optical sensor is configured to:
        capture a first image using a first subset of the photosensitive cells; and
        capture a second image using a second subset of the photosensitive cells, wherein each photosensitive cell in the second subset of photosensitive cells is different from each photosensitive cell in the first subset of photosensitive cells,
    wherein the apparatus is configured to:
        process the first image using a first optical character recognition algorithm to produce a first result; and
        process the second image using a second optical character recognition algorithm to produce a second result.

2. The medical apparatus according to claim 1, wherein the first subset of the photosensitive cells comprises alternate lines of the grid and wherein the second subset of the photosensitive cells comprises alternate lines of the grid.

3. The medical apparatus according to claim 2, wherein the first subset of the photosensitive cells comprises alternate columns of the grid and wherein the second subset of the photosensitive cells comprises alternate columns of the grid.

4. The medical apparatus according to claim 2, wherein the first subset of the photosensitive cells comprises alternate rows of the grid and wherein the second subset of the photosensitive cells comprises alternate rows of the grid.

5. The medical apparatus according to claim 1, wherein each photosensitive cell in the first subset of the photosensitive cells has distinct edges from each other photosensitive cell in the first subset of the photosensitive cells, and wherein each photosensitive cell in the second subset of the photosensitive cells has distinct edges from each other photosensitive cell in the second subset of the photosensitive cells.

6. The medical apparatus according to claim 1, wherein the optical sensor is configured to capture the first and second images simultaneously.

7. The medical apparatus according to claim 1, wherein the first character recognition algorithm produces a first confidence value in a first result and the second optical character recognition algorithms produces a second confidence value in a second result and wherein the apparatus is configured to combine the first confidence value and the second confidence value to produce a combined confidence value.

8. The medical apparatus according to claim 1, wherein the apparatus is configured to compare the first result and the second result and, when the first result and the second result are the same, to cause either of the first result and the second result to be displayed on a display of the apparatus.

9. The medical apparatus according to claim 1, wherein the apparatus is configured, if the first and second results are different, to cause the optical sensor to capture a new first image using the first subset of the photosensitive cells, and to capture a new second image using the second subset of the photosensitive cells.

10. The medical apparatus according to claim 9, wherein the apparatus is configured to:
    process the new first image using the second optical character recognition algorithm; and
    process the new second image using the first optical character recognition algorithm.

11. The medical apparatus according to claim 1, wherein the apparatus comprises a processor which is configured to process the first image and the second image using at least one optical character recognition algorithm.

12. The medical apparatus according to claim 1, wherein the apparatus is a supplementary device for attachment to a drug delivery device.

13. A method of operating a medical apparatus comprising an optical sensor having a plurality of photosensitive cells arranged in a grid, the method comprising:

capturing a first image using a first subset of the photosensitive cells;

capturing a second image using a second subset of the photosensitive cells, wherein each photosensitive cell in the second subset of photosensitive cells is different from each photosensitive cell in the first subset of photosensitive cells;

processing, by the medical apparatus, the first image using a first optical character recognition algorithm to produce a first result; and processing, by the medical apparatus, the second image using a second optical character recognition algorithm to produce a second result.

14. The method of claim 13, wherein the first subset of the photosensitive cells comprises alternate lines of the grid and wherein the second subset of the photosensitive cells comprises alternate lines of the grid.

15. The method of claim 13, wherein the optical sensor is configured to capture the first and second images simultaneously.

16. The method of claim 13, wherein the first character recognition algorithm produces a first confidence value in a first result and the second optical character recognition algorithms produces a second confidence value in a second result and wherein the apparatus is configured to combine the first confidence value and the second confidence value to produce a combined confidence value.

17. The method of claim 13, further comprising comparing the first result and the second result and, when the first result and the second result are the same, to cause either of the first result and the second result to be displayed on a display of the apparatus.

18. The method of claim 13, further comprising, in response to determining that the first and second results are different, capturing, by the optical sensor, a new first image using the first subset of the photosensitive cells, and capturing a new second image using the second subset of the photosensitive cells.

19. The method of claim 18, further comprising:
  processing the new first image using the second optical character recognition algorithm; and
  processing the new second image using the first optical character recognition algorithm.

20. The method of claim 13, wherein the apparatus comprises a processor which is configured to process the first image and the second image using at least one optical character recognition algorithm.

* * * * *